(12) United States Patent
Gullickson et al.

(10) Patent No.: US 7,682,358 B2
(45) Date of Patent: Mar. 23, 2010

(54) STEERABLE CATHETER

(75) Inventors: George Gullickson, Bloomington, MN (US); Mark T. Stewart, Lino Lakes, MN (US); Joseph E. Cardinal, Brooklyn Park, MN (US); Harry A. Puryear, Shoreview, MN (US); Scott G. Klimek, Spring Lake Park, MN (US); James R. Skarda, Lake Elmo, MN (US); Richard A. Thompson, II, Minneapolis, MN (US); Alan L. Carlson, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 1252 days.

(21) Appl. No.: 10/697,486

(22) Filed: Oct. 30, 2003

(65) Prior Publication Data

US 2005/0096590 A1 May 5, 2005

(51) Int. Cl.
*A61M 25/092* (2006.01)
(52) U.S. Cl. .................... 606/41; 606/1; 604/95.04
(58) Field of Classification Search ............. 606/41; 604/528, 95.04
See application file for complete search history.

(56) References Cited

U.S. PATENT DOCUMENTS

| 5,358,478 | A | * | 10/1994 | Thompson et al. ....... 604/95.04 |
| 5,364,351 | A | | 11/1994 | Heinzelman et al. ........ 604/95 |
| 5,891,088 | A | * | 4/1999 | Thompson et al. ....... 604/95.04 |
| 6,030,360 | A | * | 2/2000 | Biggs ..................... 604/95.01 |
| 6,530,897 | B2 | * | 3/2003 | Nardeo .................. 604/95.04 |
| 6,676,668 | B2 | * | 1/2004 | Mercereau et al. ......... 606/127 |
| 6,709,667 | B1 | * | 3/2004 | Lowe et al. ................ 424/422 |
| 2003/0093130 | A1 | | 5/2003 | Stypulkowski ............. 607/46 |
| 2003/0212394 | A1 | * | 11/2003 | Pearson et al. ............. 606/41 |

* cited by examiner

*Primary Examiner*—Michael Peffley
*Assistant Examiner*—Ronald Hupczey, Jr.

(57) ABSTRACT

A deflection mechanism for selectively inducing a bend in a catheter body includes an elongated deflection wire extending within a deflection lumen of the catheter body and into a handle. A guide track is formed within the handle and a thumb wheel is mounted proximal to the elongated guide track within the handle and supports a pinion gear; the thumb wheel and the pinion gear are adapted to be rotated about a common thumb wheel axis, which extends substantially perpendicular to the longitudinal axis. A rack arm extends obliquely to the longitudinal axis of the handle and includes runners received by the guide track, an attachment point coupling the deflection wire to the rack arm and a linear rack engaging the pinion gear. Rotation of the thumb wheel in a first direction draws the deflection wire proximally through the deflection lumen.

29 Claims, 7 Drawing Sheets

STEERABLE CATHETER

FIELD OF THE INVENTION

The present invention relates generally to steerable catheters, and more specifically to steerable electrophysiology catheters for use in mapping and/or ablation of accessory pathways in myocardial tissue of the heart wall.

BACKGROUND OF THE INVENTION

Many elongated medical devices are known that are inserted through an access pathway into a body vessel, organ or cavity to locate a therapeutic or diagnostic distal segment of the elongated medical device into alignment with an anatomic feature of interest. For example, catheters, introducers and guide sheaths of various types, drainage tubes, and cannulae are available that extend from outside the body through an access pathway to a site of interest and provide a lumen through which fluids, materials, or other elongated medical devices are introduced to the site or body fluids are drained or sampled from the site.

Such elongated medical devices must have flexibility to navigate the twists and turns of the access pathway, sufficient column strength in the proximal segment thereof to be pushed through the access pathway alone or over a guidewire or through a lumen, and the capability of orienting the distal segment and any electrodes or sensors or ports of the distal segment in a preferred alignment with an anatomical feature at the accessed site so that a diagnostic or therapeutic procedure can be completed. In general terms, the elongated medical device body must also resist kinking and be capable of being advanced through access pathways that twist and turn, sometimes abruptly at acute angles.

The distal segments of such elongated medical devices frequently need to be selectively deflected or bent and straightened again while being advanced within the patient to steer the catheter body distal end into a desired body lumen or chamber. Various steerable mechanisms have been disclosed to steer catheters and other elongated medical devices, e.g., steerable guidewires and stylets, that involving use of a deflection mechanism extending through a deflection lumen of the catheter body to an attachment point in the catheter body distal segment. Typically, elongated wires variously referred to as control lines or reins or deflection wires or traction wires or push-pull wires or pull wires (herein "deflection wires" unless otherwise specified), extending between a proximal control mechanism and the distal attachment point. More complex steerable catheters have two or more deflection lumens and deflection wires extending from the handle through the deflection wire lumens to different points along the length or about the circumference of the catheter body to induce bends in multiple segments of the catheter body and/or in different directions. The deflection lumens extend parallel to the central catheter body axis. In many cases, a handle is attached at the elongated catheter body proximal end, and the proximal end(s) of the deflection wire(s) is coupled to movable control(s) on the handle that the user manipulates to selectively deflect or straighten the distal segment and, in some cases, intermediate segments of the catheter body.

Many versions of electrophysiology (EP) catheters have been disclosed that are designed to perform mapping and/or ablation of cardiac tissue to diagnose and treat abnormal tissue that induces or sustains cardiac arrhythmias and that employ deflectable distal and intermediate segments controlled by deflection wire mechanisms. During an EP ablation or mapping procedure, the guide catheter must be maneuvered through a patient's branched vasculature to advance an EP device into a patient's coronary sinus. The steerable distal end of the guide catheter is used to orient the distal tip of the EP device with respect to tissue, such as a patient's endocardium, to facilitate proper delivery of the device's RF or ablation energy to the tissue. Highly complex shapes are sometimes found necessary to encircle a pulmonary vein orifice, for example, to ablate the left atrial wall tissue to interrupt arrhythmic pathways.

There remains a need for an ergonomic handle incorporating an effective and easy to use deflection mechanism.

BRIEF DESCRIPTION OF THE DRAWINGS

The following drawings are of particular embodiments of the invention and therefore do not limit its scope, but are presented to assist in providing a proper understanding of the invention. The drawings are not to scale (unless so stated) and are intended for use in conjunction with the explanations in the following detailed description. The present invention will hereinafter be described in conjunction with the appended drawings, wherein like numerals denote like elements, and:

FIG. 1 is a perspective view of an EP mapping and/or ablation catheter according to one embodiment of the present invention;

FIG. 2 is an enlarged plan view of one side of the handle of the EP catheter of FIG. 1;

FIG. 3 is an enlarged plan view of another side of the handle of the EP catheter of FIG. 1;

FIGS. 4A-B are cross-section views taken along section line 4-4 of FIG. 3;

FIG. 5 is a perspective view of an interior of the handle of the EP catheter of FIG. 1;

FIG. 6 is a perspective view of a rack arm component depicted in FIG. 5;

FIG. 7 is a perspective view of an interior of a thumb wheel component depicted in FIG. 5;

FIG. 8 is a perspective view of an exterior of the thumb wheel component shown in FIG. 7;

FIG. 9 is a perspective view of an exterior of another thumb wheel component adapted to mate with the thumb wheel component shown in FIGS. 7 and 8; and FIG. 10 is an enlarged side view of the handle of the EP catheter of FIG. 1.

DETAILED DESCRIPTION

The following detailed description is exemplary in nature and is not intended to limit the scope, applicability, or configuration of the invention in any way. Rather, the following description provides a practical illustration for implementing exemplary embodiments of the invention.

The present invention is preferably embodied in a steerable catheter comprising an elongated catheter body having a deflectable catheter body distal segment and an ergonomically shaped handle adapted to be grasped in use of the steerable catheter. A particular example of such a steerable catheter as described herein as an EP catheter 10 including an elongated catheter body 20 and a handle 40. However, it will be understood that the present invention can be practiced in other steerable catheters used to access a site in the body.

As shown in FIG. 1, catheter body 20 extends between a catheter body distal end 26 and a catheter body proximal end located within a strain relief 28 and includes a proximal segment 23 joined at a mutual junction with a deflectable distal segment 27. The proximal segment 23 has sufficient column strength and is capable of good torque transmission to permit controlled placement of distal segment 27 at a target site in a body. A deflection lumen 12 (FIG. 5) extends from the proximal end to the distal segment 27 accommodating an elongated deflection wire 21 extends from a wire distal end coupled to the catheter body distal segment 27 proximally to a wire proximal end within handle 40.

Figure 1:
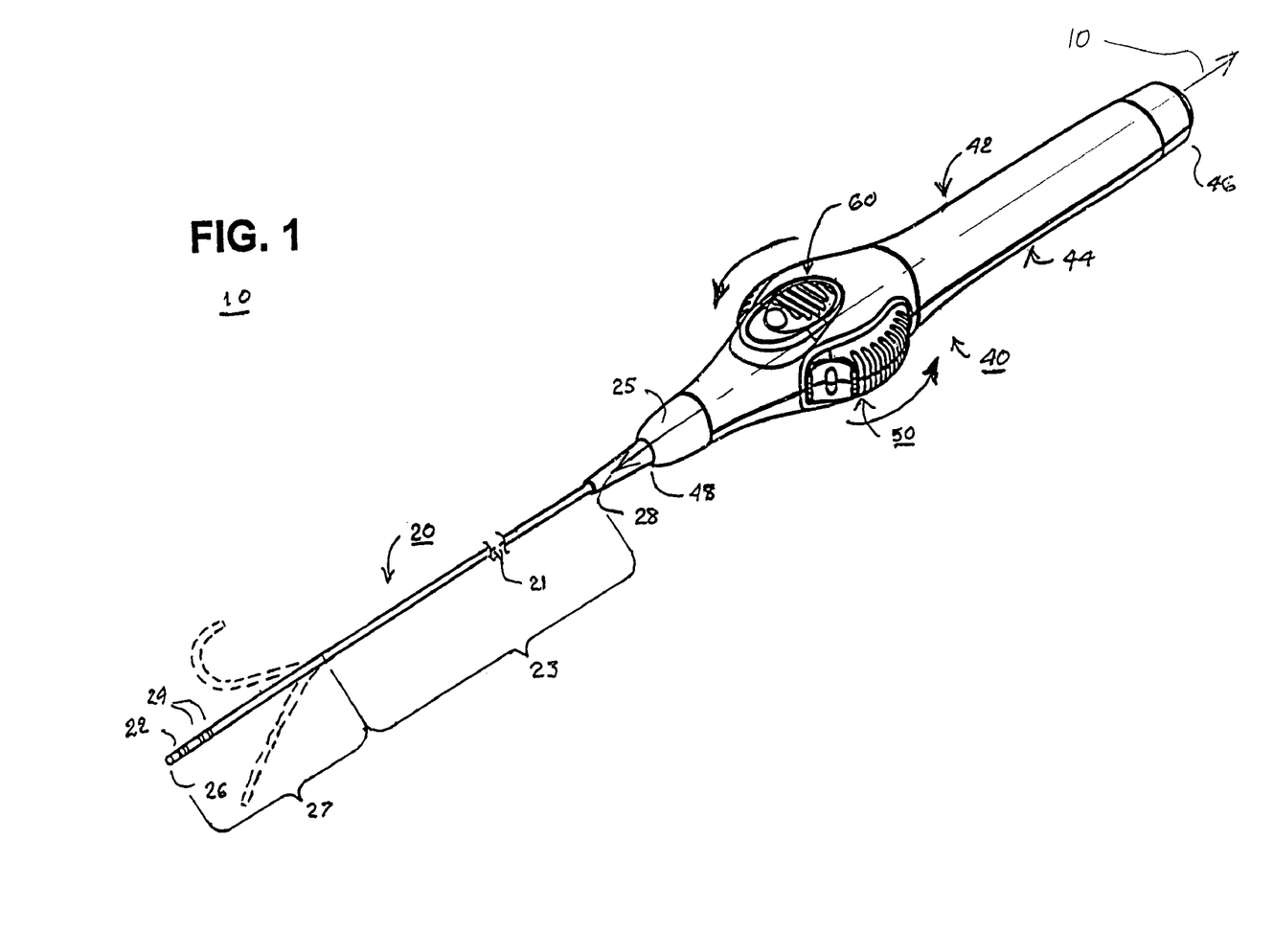

FIG. 1 further illustrates catheter body 20 supporting an ablation electrode 22 and one or more mapping electrodes 24 coupled to catheter body distal segment 27. It will be understood that electrical conductors are enclosed within catheter body 20, which extend from electrodes 22 and 24 proximally through catheter body 20 and further extend through handle 40 to an electrical connector (not shown) included on handle 40. According to one embodiment, catheter body 20 has a uniform outside diameter of about 0.052 inch (1.32 mm) to 0.1040 inch (2.64 mm) and a length of about 50 cm to 110 cm. The catheter body 20 can take any of the forms known in the art of steerable EP mapping and/or ablation catheters.

Figure 4A:
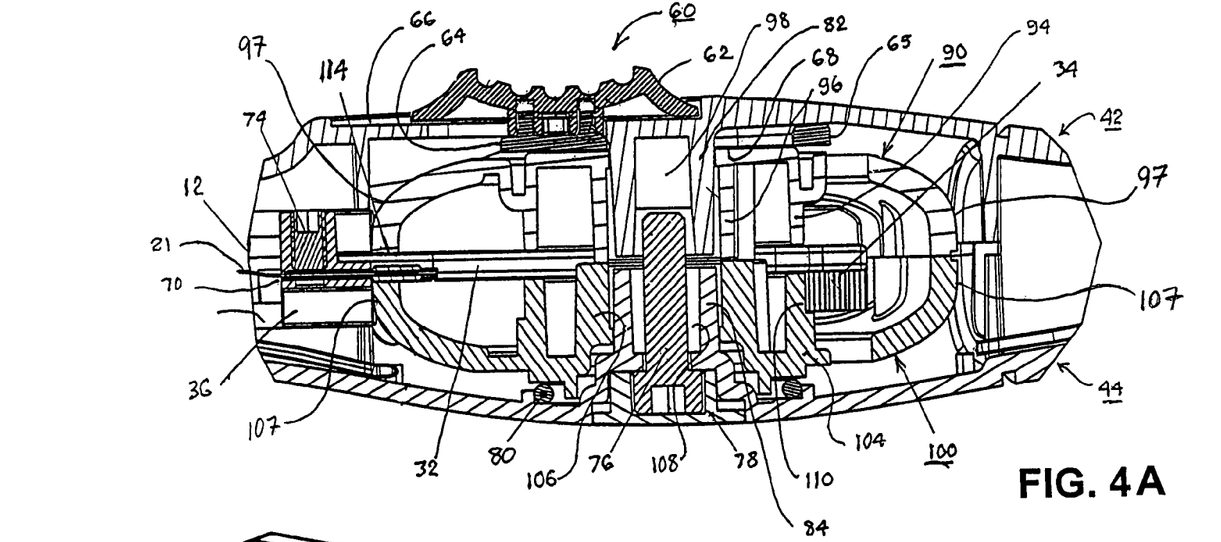
Figure 5:
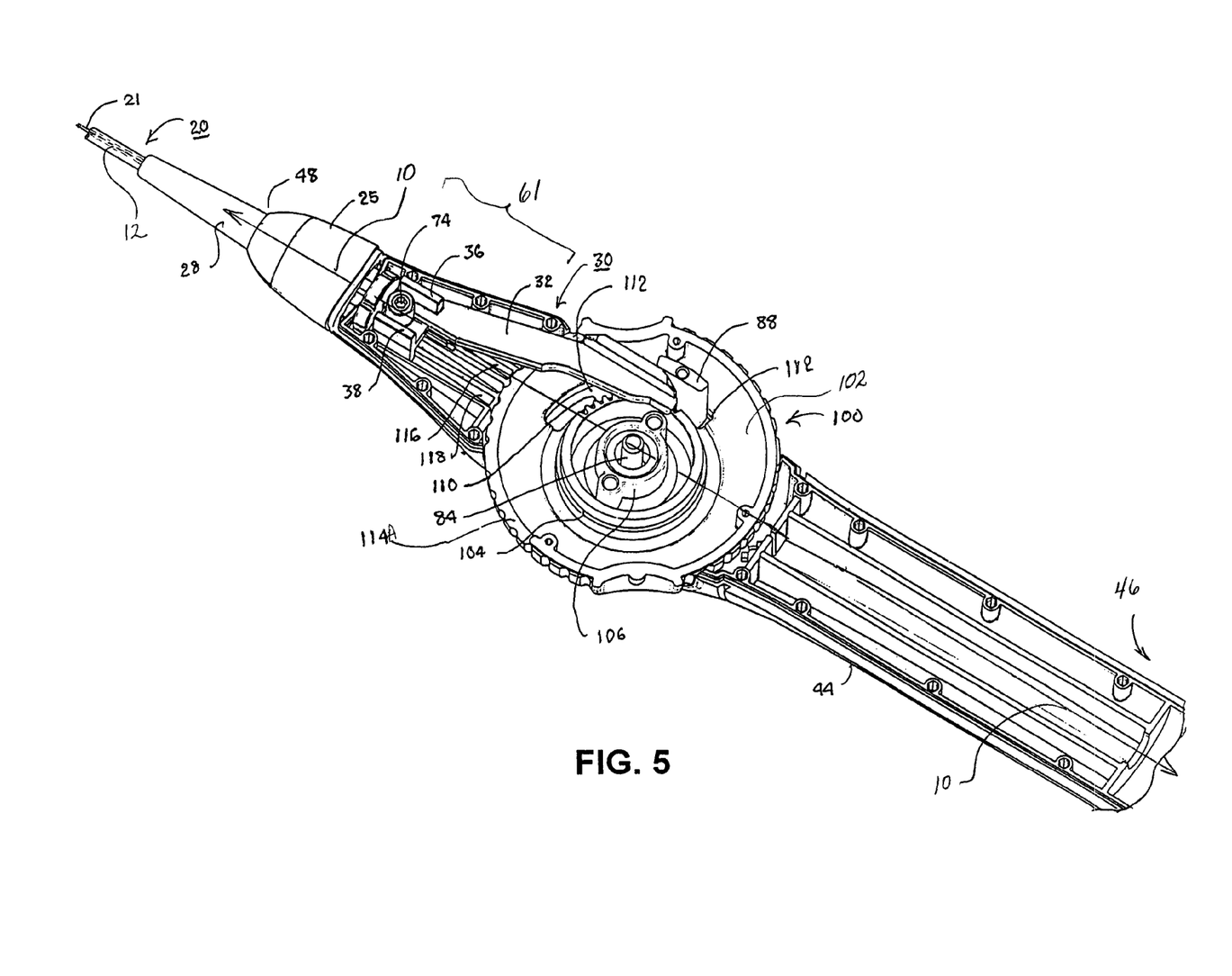

According to one embodiment of the present invention, as illustrated by arrows in FIG. 1, a thumb wheel 50 of handle 40 (that is coupled to the deflection wire proximal end through a rack arm 30 as shown in FIGS. 4A and 5) is rotated from a neutral position to pull deflection wire 21 and induce a J-shape bend in the off-axis direction (illustrated in broken lines). It will be understood that thumb wheel 50 may also be rotated in an opposite direction to push the deflection wire 21 inducing a less pronounced curve or bend in the push direction opposite to the pull direction (illustrated in broken lines). Thus, the deflection wire 21 can be a push-pull wire as illustrated or simply can function as a pull wire.

As shown in FIGS. 1 and 5, handle 40, which is adapted for ergonomic handling of the steerable catheter 10, extends from a handle proximal end 46 to a handle distal end 48 along a longitudinal axis 10. According to the illustrated embodiment, strain relief 28 enclosing the catheter body proximal end is received within a bore of the handle distal end 48 substantially aligning handle axis 10 with a longitudinal axis of the catheter body 20; a conical fitting 25 fits over and entraps a proximal portion of the strain relief 28. An electrical connector for making connection with a cable can be formed at handle proximal end 46.

Figure 2:
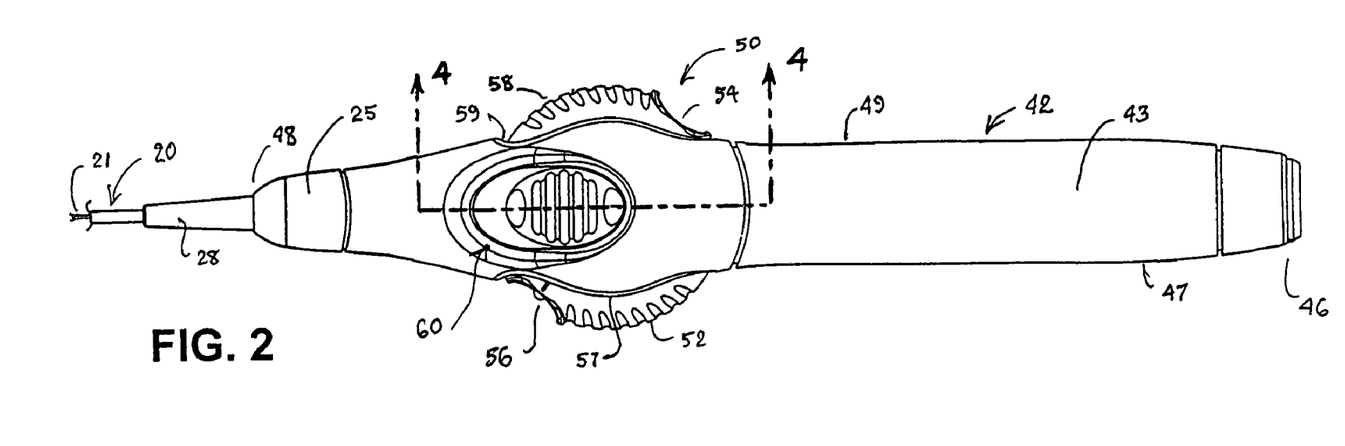
Figure 3:
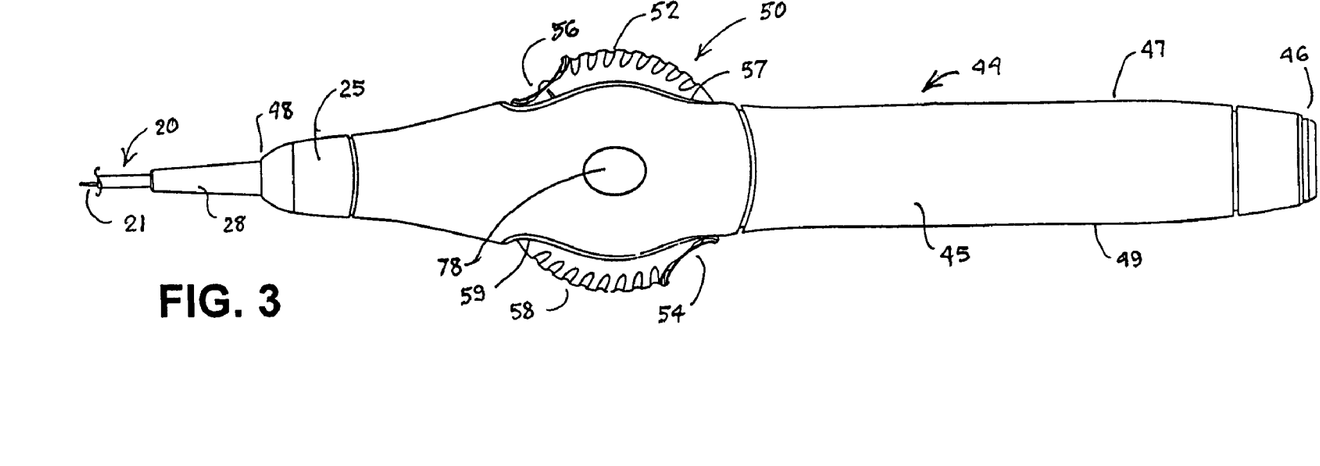

FIGS. 2 and 3 illustrate handle 40 formed of a first handle body portion 42 joined to a second handle body portion 44 extending between handle proximal end 46 and handle distal end 48, according to one embodiment of the present invention; according to alternate embodiments handle body portions 42 and 46 are integrally formed. FIGS. 2 and 3 further illustrate handle 40 including first and second major sides 43 and 45 and first and second minor sides 47 and 49; rotatable thumb wheel 50 is supported by the handle 40, intermediate first and second major sides 43 and 45, wherein a first exposed thumb wheel section including serrations 52 and an indentation 56 extends through a first thumb wheel window 57 in first minor side 47 and a second exposed thumb wheel section also including serrations 54 and an indentation 58 extends through a second thumb wheel window 59 in the second minor side 49. According to alternate embodiments, thumb wheel is exposed on a single side through a single window. According to embodiments of the present invention, thumb wheel 50 is adapted to be rotated about a thumb wheel axle (82 and 84, FIGS. 4A-B), extending transversely to the axis 10 of the handle 40, from a neutral position to a selected pull or retracted and a push or advanced position.

Figure 7:
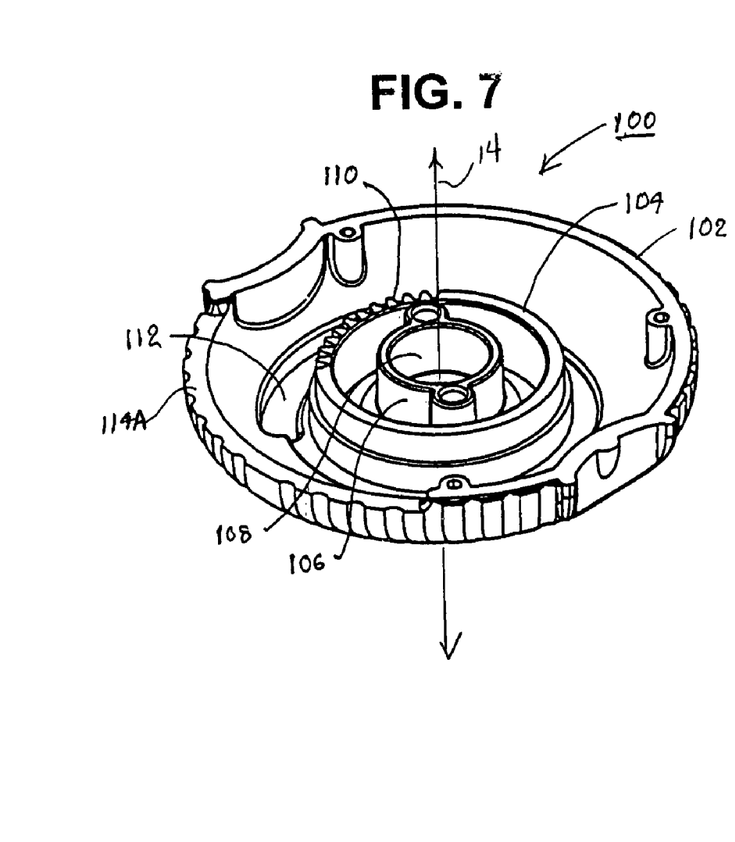
Figure 8:
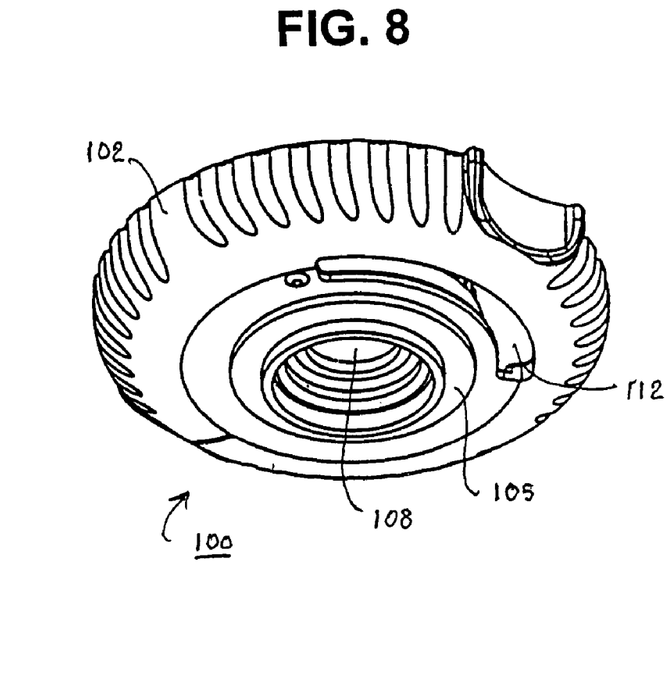

FIGS. 4A-B, and 7-9 illustrate thumb wheel 50 including first and second thumb wheel sidewalls 90 and 100 to be joined together along a plane substantially perpendicular to a thumb wheel axis 14 (FIG. 7), according to one embodiment of the present invention. As shown in FIGS. 4A, 5 and 7, second thumb wheel sidewall 100 includes a central axis bore 108 about which first and second concentric, internal axial extensions or rings 104 and 106 are formed. According to an embodiment of the present invention, as illustrated in FIG. 7, first internal axial extension 104 is formed with the outwardly extending teeth of a pinion gear 110. As further illustrated in FIG. 7, an arcuate opening 112 is formed through wheel sidewall 100 extending alongside the pinion gear 110. An O-ring boss 105 is formed around an outward extension of the first internal axial extension 104 as shown in FIG. 8. An outer rim 102 of the wheel sidewall 100 is substantially at the same height as second internal axial extension 106 except for a notch 114A, which is substantially at the same height as the first internal axial extension 104, formed along a portion of the outer rim 102 as shown in FIG. 7.

Figure 6:
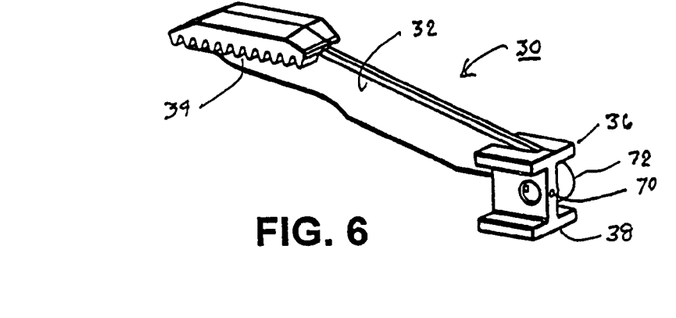

In a further aspect of the invention, a rack arm 30 depicted in FIGS. 4A, 5 and 6 is coupled to the proximal end of the deflection wire 21 and cooperates with the pinion gear 110 of the second thumb wheel sidewall 100. Rack arm 30 includes an arm bar 32 that extends between a rack arm proximal end formed with teeth of a linear rack 34 and a rack arm distal end formed with runners 36 and 38 and a mechanism for attachment with the proximal end of the deflection wire 21. A distal handle segment 61 of handle 40 is formed with an elongated linear track aligned substantially with the axis 10 of the handle 40, the linear track defined by track sides 116 and 118 and adapted to receive runners 36 and 38 of rack arm 30; thus, according to embodiments of the present invention, rack arm 30 extends obliquely to handle axis 10 from runners 36 and 38 engaged in the track to linear rack 34 engaging pinion gear 110. It will be understood that the interior of the first handle body portion 42 is also shaped having a linear track bounded by track sides.

FIG. 6 further illustrates the distal end of the rack arm 30 H-shaped to define the runners 36 and 38 separated apart by bridge that incorporates an axially extending bore 70 for receiving the deflection wire 21. Runners 36 and 38 define four corner edges that engage the four track corners or sides formed in the first and second handle body portions 42 and 44. It will be understood that the runners and track can be shaped in a variety of ways without departing from the spirit and scope of the invention.

Figure 9:
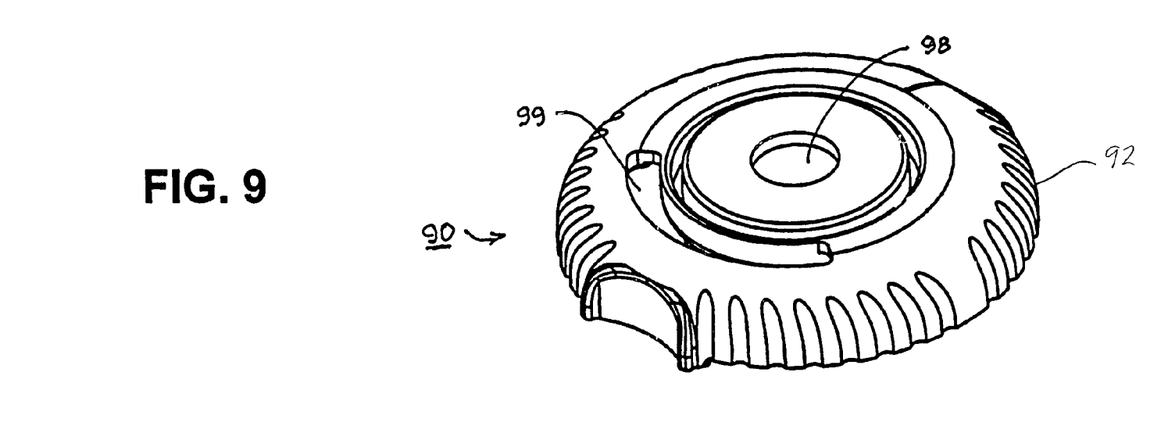

As shown in FIGS. 4A and 9, the first thumb wheel sidewall 90, formed in a similar manner to second thumb wheel sidewall 100, including a central axis bore 98, first and second concentric, internal axial extensions or rings 94 and 96, respectively, an arcuate opening 91 and a notch (obscured in the view) that is formed along a portion of an outer rim 92 of wheel sidewall 90. It will be understood that a notch, not shown, formed along the edge of outer rim 92 is aligned with the notch 114A shown in FIG. 7 to form a circumferentially extending slot 114, when the first and second wheel sidewalls 90 and 100 are assembled together, through which rack arm 30 extends (FIG. 4A).

FIG. 4A further illustrates first internal axial extension 94 extending inwardly in alignment with, but spaced apart from, the first internal axial extension 104 that is formed with the outwardly extending teeth of a pinion gear 110. The central axis bore 98 is defined within the second internal axial extension 96. The second internal axial extension 96 extends inwardly as shown in FIG. 4A in alignment with and into engagement with the second internal axial extension 106. An arcuate opening 91 is formed through the wheel sidewall 90 extending alongside the first internal axial extension 96 that is aligned with the arcuate opening 112 when the first and second wheel sidewalls 90 and 100 are assembled together.

Figure 4B:
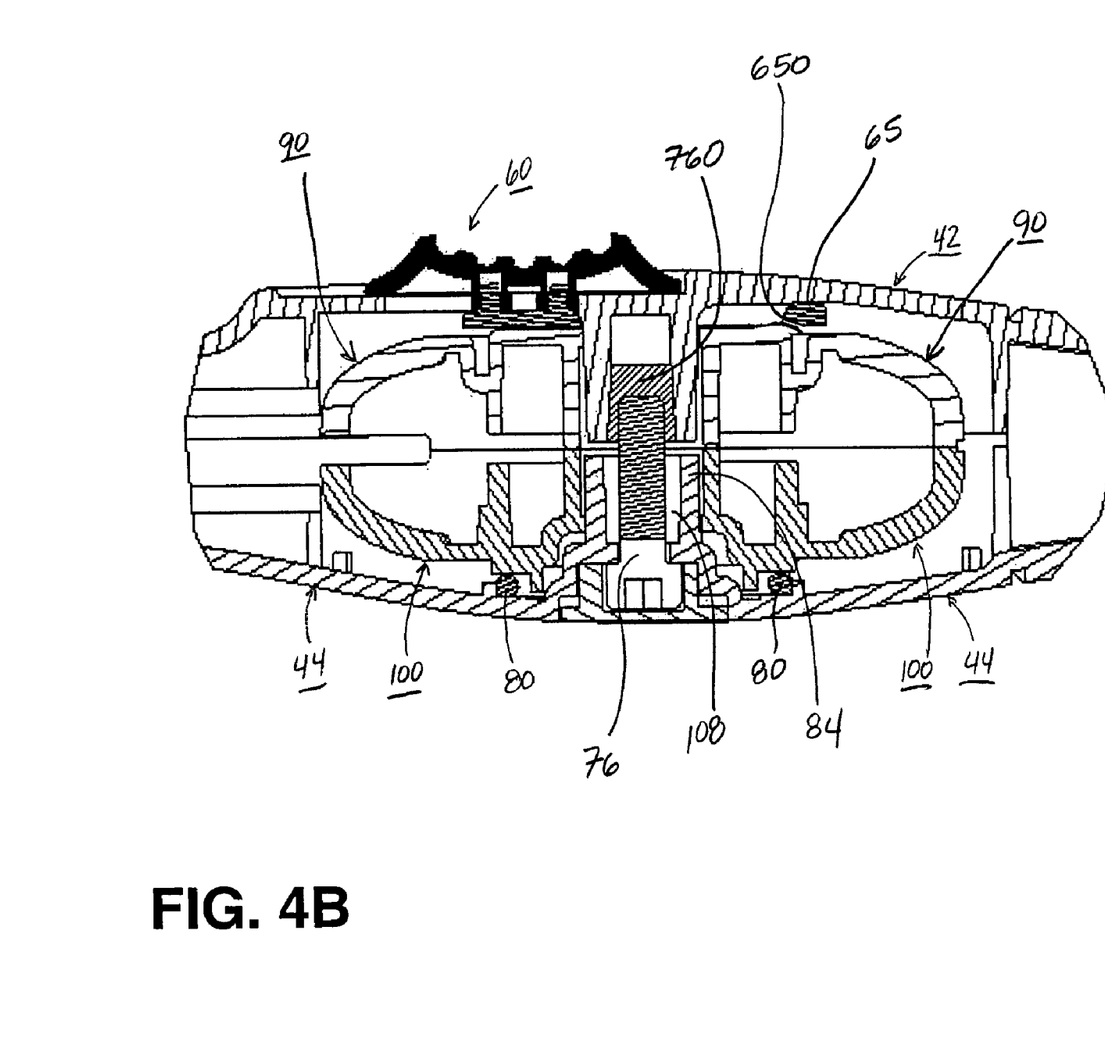

As shown in FIGS. 4A-B and 5, the second wheel sidewall 100 is fitted into engagement with the second handle body portion 44 so that axle 84 extends inwardly from second handle body portion 44 through central axis bore 108, and second wheel sidewall 100 rests against an O-ring 80. A guide 88 extends inwardly from the second handle body portion 44 through the arcuate opening 112 so that a space is defined between the teeth of the pinion gear 110 and the guide 88. It will be understood the guide 88 bears against a matching guide that extends inwardly from the first handle body portion 42 and through the arcuate opening 99 of the first wheel sidewall 90. According to the illustrated embodiments, guide 88 and the matching guide, fitting through the arcuate openings 112 and 99, respectively, hold linear rack 34 of rack arm 30 against pinion gear 110; according to alternate embodiments, an internal feature of thumb wheel 50 may perform the same function.

In a further aspect of the invention, a friction application mechanism is selectively engageable in use to apply force laterally to thumb wheel 50 maintaining thumb wheel 50 in a selected position. The friction engaging mechanism includes a thumb slide 60 that can be retracted proximally within a thumb slide window 66 (FIG. 4A). The friction engaging mechanism extends in part through first major side 43 of first handle body portion 42 to apply force laterally to the thumb wheel 50 to maintain the thumb wheel 50 rotated into a selected position as described further below.

In FIGS. 4A-B, it will be noted that O-ring 80 is fitted into a groove around an axle 84 that extends inwardly from the second handle body portion 44. According to one embodiment, O-ring 80 functions as a resilient compressible member that is disposed between the thumb wheel 50 and the second handle body portion 44. O-ring 80 is compressed as the thumb wheel 50 is pressed against it to inhibit movement of the thumb wheel 50. A thumb slide 62 of slide mechanism 60 extends through the friction window 66 formed through the first major side 43 of the first handle body portion 42 as shown in FIGS. 4A-B. Thumb slide 62 can be retracted proximally to apply force laterally to thumb wheel 50 to move it against and compress O-ring 80 to maintain thumb wheel 50 rotated into a selected position.

According to the illustrated embodiment, thumb slide 62 is attached to an elongated ring 64 having an elongated opening through which inwardly extending first axle 82 extends. Thumb slide 62 and elongated ring 64 are normally disposed proximally as shown in FIGS. 2 and 4A allowing rotation of thumb wheel 50 about the transversely extending axis. A proximal portion 65 of elongated ring 64 is thicker than a distal portion of elongated ring 64 so that, when thumb slide 62 is moved distally along window 66, the thickened proximal portion 65 is interposed between first wheel sidewall 90 and first handle body portion 42 pressing second wheel sidewall 100 against O-ring 80. According to one embodiment interfacing surfaces of thickened proximal portion 65 and first wheel sidewall 90 include opposing tapers 650 to facilitate smooth movement of thumb slide 62. The compression of O-ring 80 frictionally retains the thumb wheel 50 in a desired rotary position to maintain a curve drawn in the catheter body distal segment 27 until thumb slide 62 is engaged to move ring 64 distally to the release position. In this way, thumb wheel 50 is fixed in a selected retracted or extended position or released to return to the neutral position.

FIG. 4B further illustrates a threaded pin 76 extending, within thumb wheel axel 84 of second handle body portion 44, through central axis bore 108 of second thumb wheel sidewall 100. Pin 76 engages a mating insert 760 held within thumb wheel axis 82 of first handle body portion 42. According to one embodiment of the present invention, a depth to which pin 76 is engaged within insert 760 may be adjusted as means to adjust a gap, wherein O-ring 80 is disposed, between second thumb wheel sidewall 100 and second handle body portion 44, thereby tuning a frictional force against which thumb wheel 50 is freely rotated along with the force required to retract thumb slide 62, which secures thumb wheel 50 in a selected position.

Figure 10:
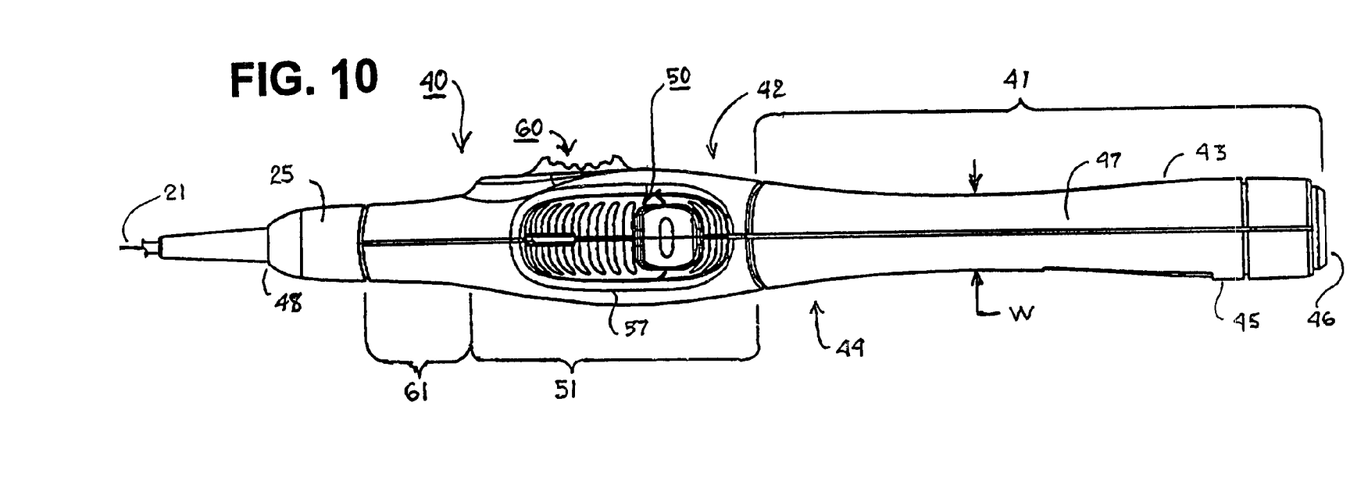

FIG. 10 is an enlarged side view of handle 40 wherein a thumb wheel support segment 51 is illustrated intermediate a proximal grasping segment 41 extending proximally to handle proximal end 46 and a distal handle segment 61 extending distally to distal handle end 48. According to one embodiment of the present invention, proximal grasping segment 41 is adapted to be grasped between the fingers and the palm of the user so that the user's thumb can selectively engage the first and section exposed thumb wheel sections 52, 56 and 54, 58 and/or the thumb slide 60. The handle grasping segment 41 is ergonomically shaped having the first and second opposed major sides 43 and 45 separated by the first and second opposed minor sides 47 and 49 whereby a handle thickness is defined by the width of the first and second minor sides 47 and 49. A minimum thickness Is defined within handle grasping segment 41 between the handle proximal end 46 and the thumb wheel support segment 51. The handle thickness is gradually reduced distally from the handle proximal end 46 toward the thumb wheel support segment 51 to the minimum thickness and is gradually reduced proximally from the thumb wheel support segment 51 toward the handle distal end 46 to the minimum thickness, thereby defining a narrowed waist W within the handle grasping segment 41. In use, the handle grasping segment fits in the user's palm with the thumb wheel 50 aligned to the user's thumb and the narrowed waist W enhances the ergonomic feel of the handle 40. In selecting a material for handle body portions 42, 44 rigidity, toughness and dimensional stability over a relatively large area of handle 40 should be considered.

In assembly, the strain relief 28 is fitted to the distal end of the second handle body portion 44, and the electrical conductors are routed through the distal segment 61, the wheel mounting segment 51, and the handle grasping segment 41 for attachment to electrical connector terminals. The O-ring 80 and second wheel sidewall 100 are then fitted into the second handle body portion 44. The untrimmed deflection wire 21 may be passed through the bore 70.

In one approach, the linear rack 34 is fitted between the pinion gear 110 and the guide 88 with the teeth of linear rack 34 fitted into engagement with the teeth of the pinion gear 110. The runners 36 and 38 are at the same time inserted into the track defined by the track sides 116 and 118. The arm bar 32 then extends across the notch 114A and over the edge of the first internal axial extension 104. The second wheel sidewall 100 is rotated to move the runners 36 and 38 along the elongated guide track formed within the handle in substantial alignment with the axis 10 extending from an elongated guide track proximal end and an elongated guide track distal end.

The maximal axial proximal and distal movement of the runners 36 and 38 within the track defined by the track sides 116 and 118 upon rotation of the second wheel sidewall 100 can be obtained by proper alignment of the teeth of the linear rack 34 with the teeth of the pinion gear 110. The first wheel sidewall 90 is then fitted over the second wheel sidewall 100 after proper alignment is obtained, so that the linear rack 34 is trapped within the assembled thumb wheel 50.

In an alternative approach, the first wheel sidewall 90 can be fitted to the second wheel sidewall 100 with the linear rack 34 located inside the first and second wheel sidewalls 90 and 100. The assembly can then be mounted to the second handle body portion 44 by fitting the teeth of the linear rack 34 into engagement with the teeth of the pinion gear 110. The assembly is then fitted over the axle 84 and the runners 36 and 38 are inserted into the track defined by the track sides 116 and 118.

At this point, the deflection wire 21 extends through the axial bore 70 through the distal end of the rack arm 30. A set screw 74 or the like extending through a threaded transverse screw bore 72 is tightened against the deflection wire 21 extending through the bore 70 to fix the deflection wire 21 to the distal end of the rack arm. The distally extending portion of the deflection wire 21 can then be trimmed. In selecting a material for rack 30, not only strength but properties facilitating incorporation of a threaded interface for set screw 74 should be considered.

The friction engaging mechanism described herein above is then assembled to the first handle body portion 42. The assembly of the first handle body portion 42 and friction engaging mechanism is applied against the assembled push button 50 and the edge of the second handle portion 44 to couple the first and second handle body portions 42 and 44 together. As shown in FIG. 4, an inwardly extending first axle 82 of the first handle body portion 42 extends through the bore 98 of the first wheel sidewall 90. Pin 76 is extended through the bore of the second axle 84 and into the bore of the first axle 82 and a cap 78 is fitted over the pin 76 to lock it in place. The wheel 50 is thereby supported to be manually grasped and rotated to move the linear rack 34 parallel to the handle axis 10 and the distal end runners 36 and 38 along the guide track and push or pull the deflection wire 21 through the deflection lumen 12 to induce a bend within the catheter body distal segment 27.

A selection of materials, according to a preferred embodiment of the present invention, from which particular parts of handle 40 are formed, is presented in Table 1, wherein item numbers from the Figures are incorporated for reference.

TABLE 1

| Part/item number | Exemplary Material |
| --- | --- |
| Handle body portions/42, 44 | Polycarbonate |
| Rack/30 | Polyetherimide |
| Set screw/74 | Stainless Steel |
| Wheel sidewalls/90, 100 | ABS |
| Thumb slide/60 | Polycarbonate |
| Elongated ring/64 | Nylon |
| O-ring/80 | Teflon impregnated fluoroelastomer |

According to some embodiments of the present invention materials forming handle body portions 42, 44 and rack 30 should be dissimilar while having a substantially similar hardness for smooth passage, without gouging, of runners 36 along linear track defined by track sides 116 and 118. Additionally, according to some embodiments, a material forming elongated ring 64 should have a low coefficient of friction and be dissimilar to the material forming portions 42, 44 and thumb wheel sidewalls 90, 100. Furthermore, according to some embodiments, a material forming O-ring 80 should be compressible with a low coefficient of friction and not graze at interfaces with handle body portion 44 and thumb wheel sidewall 100. Finally, a material forming thumb slide is preferably the same as that forming handle body portions 42, 44.

In addition to the materials listed in Table 1, a material providing superior tactile qualities to improve contact friction between handle 40 and a gloved hand of an operator may be included as a coating over outer surfaces of handle body portions 42, 44 and exposed outer surfaces of thumb wheel sidewalls 90, 100; an example of such a material is Styrene Ethylene Butadiene Styrene (SEBS) or Versaflex.

It will be understood that certain of the above-described structures, functions and operations of the above-described preferred embodiments are not necessary to practice the present invention and are included in the description simply for completeness of an exemplary embodiment or embodiments. In addition, it will be understood that specifically described structures, functions and operations set forth in the above-referenced patents can be practiced in conjunction with the present invention, but they are not essential to its practice. It is therefore to be understood, that within the scope of the appended claims, the invention may be practiced otherwise than as specifically described without actually departing from the spirit and scope of the present invention.

What is claimed is:

1. A steerable catheter comprising:
    an elongated catheter body including a proximal end, a distal segment and a deflection lumen extending from the proximal end toward the distal segment;
    a handle coupled to the catheter body proximal end and including a longitudinal axis; and
    a deflection mechanism for selectively inducing a bend in the catheter body; the deflection mechanism comprising:
        an elongated deflection wire extending within the deflection lumen of the catheter body and into the handle;
        a guide track formed within the handle in substantial alignment with the longitudinal axis;
        a thumb wheel mounted proximal to the guide track within the handle and supporting a pinion gear, the thumb wheel and pinion gear adapted to be rotated about a common thumb wheel axis, which extends substantially perpendicular to the longitudinal axis; and
        a rack arm including runners received by the guide track, an attachment point coupling the deflection wire to the rack arm and a linear rack engaging the pinion gear; the rack arm extending within the handle, obliquely to the longitudinal axis, from the runners to the linear rack, the attachment point being movable along a linear path that is substantially aligned with the deflection lumen;
    wherein rotation of the thumb wheel in a first direction moves the linear rack proximally, via the engagement of the linear rack with the pinion gear, to draw the deflection wire proximally through the deflection lumen and along the guide track inducing a first bend of the catheter body.

2. The catheter of claim 1, wherein rotation of the thumb wheel in a second direction moves the linear rack distally, via the engagement of the linear rack with the pinion gear, to push the deflection wire along the guide track and through the deflection lumen inducing a second bend of the catheter body.

3. The catheter of claim 1, wherein the handle further includes a first major side and a second major side and the thumb wheel is disposed intermediate the first major side and the second major side.

4. The catheter of claim 3, wherein the deflection mechanism further comprises a securing mechanism selectively engageable in use from either he first major side or the second major side of the handle to apply a friction force, which holds the thumb wheel preventing further rotation of the thumb wheel.

5. The catheter of claim 4, wherein the thumb wheel includes a sidewall and the securing mechanism comprises a resilient compressible member disposed in a gap between the thumb wheel sidewall and one of the first major side and the second major side of the handle body.

6. The catheter of claim 5, wherein one of the first major side and the second major side of the handle includes a window and a thumb slide extending therethrough; the thumb slide adapted to apply a lateral force pushing the thumb wheel against the resilient compressible member thereby engaging the securing mechanism.

7. The catheter of claim 6, wherein the securing mechanism further includes an elongated ring coupled to the thumb slide whereby the thumb slide applies the lateral force by wedging the elongated ring between the thumb wheel and one of the first major side and the second major side of the handle.

8. The catheter of claim 5, further comprising means to adjust the gap between the thumb wheel sidewall and the one of the first major side and the second major side of the handle body.

9. The catheter of claim 3, wherein the handle further includes a first minor side extending between the first major side and the second major side and a first thumb wheel window extending through the first minor side through which a portion of the thumb wheel is exposed.

10. The catheter of claim 9, wherein the thumb wheel includes a sidewall forming an outer rim; the outer rim being exposed through the first thumb wheel window.

11. The catheter of claim 10, wherein the outer rim includes serrations.

12. The catheter of claim 10, wherein the outer rim includes an indentation.

13. The catheter of claim 9, wherein the handle further includes a second minor side, opposite the first minor side, and a second thumb wheel window extending through the second minor side through which a second portion of the thumb wheel is exposed.

14. The catheter of claim 13, wherein the thumb wheel includes a sidewall forming an outer rim; the outer rim exposed through the first and second thumb wheel windows.

15. The catheter of claim 14, wherein the outer rim includes serrations.

16. The catheter of claim 14, wherein the outer rim includes a first indentation exposed through the first thumb wheel window and a second indentation exposed through the second thumb wheel window; the first and second indentations adapted to engage a thumb and a finger of an operator.

17. The catheter of claim 1, wherein the handle further includes a first handle body portion and a second handle body portion joined along a plane substantially perpendicular to the thumb wheel axis; the first handle body portion and the second handle body portion capturing the thumb wheel there between.

18. The catheter of claim 1, wherein
the thumb wheel includes an internal axial extension, a sidewall forming an outer rim and a circumferentially extending slot through the outer rim of the sidewall; and
the pinion gear is formed on the internal axial extension and the rack arm extends through the circumferentially extending slot to engage the pinion gear.

19. The catheter of claim 1, wherein
the thumb wheel includes a sidewall and an arcuate opening extending therethrough;
the handle includes an inwardly extending guide passing through the arcuate opening holding the linear rack of the rack arm against the pinion gear of the thumb wheel.

20. The catheter of claim 1, wherein
the thumb wheel includes a first sidewall and a second sidewall joined along a longitudinal plane substantially perpendicular to the thumb wheel axis;
the junction of the first sidewall and the second sidewall forming a circumferentially extending slot through which the rack arm extends; and
the first sidewall including an internal axially extension upon which the pinion gear is formed.

21. The catheter of claim 20, wherein
the first sidewall and the second sidewall each include an arcuate opening extending therethrough; and
the handle includes an inwardly extending guide passing through the arcuate openings holding the linear rack of the rack arm against the pinion gear of the thumb wheel.

22. The catheter of claim 1, wherein the guide track includes track sides engaging the runners of the rack arm.

23. The catheter of claim 22, wherein the rack arm includes an H-shaped cross-section defining the runners.

24. The catheter of claim 1, wherein the handle includes a first major side and a second major side; the first and second major sides forming a thumb wheel support segment and a grasping segment extending proximally from the support segment; the grasping segment including a narrowed waist facilitating ergonomic handling.

25. The catheter of claim 24, wherein the thumb wheel is disposed intermediate the first major side and the second major side.

26. The catheter of claim 24, wherein the first and second major sides are formed by a first handle body portion and a second handle body portion joined along a plane substantially perpendicular to the thumb wheel axis; the first handle body portion and the second handle body portion capturing the thumb wheel there between.

27. The steerable catheter of claim 1 wherein the obliquely-extending rack arm positions the linear rack parallel to the longitudinal axis.

28. The steerable catheter of claim 27 wherein the guide track comprises a pair of track sides formed along a distal handle segment.

29. A steerable catheter comprising:
an elongated catheter body including a proximal end, a distal segment and a deflection lumen extending from the proximal end toward the distal segment;
a handle coupled to the catheter body proximal end and including a longitudinal axis and an inwardly extending stationary guide; and
a deflection mechanism for selectively inducing a bend in the catheter body; the deflection mechanism comprising:
an elongated deflection wire extending within the deflection lumen of the catheter body and into the handle;
a guide track formed within the handle in alignment with the longitudinal axis;
a thumb wheel mounted proximal to the guide track within the handle, the thumb wheel comprising
an internal axial extension having a circumferential surface offset from the longitudinal axis,
a sidewall forming an outer rim and a circumferentially extending slot through the outer rim of the sidewall, and
a pinion gear formed along a portion of the circumferential surface of the internal axial extension;
the thumb wheel adapted to be rotated to cause rotation of the pinion gear about a common thumb wheel axis, which extends substantially perpendicular to the longitudinal axis; and a rack arm comprising runners received by the guide track, an attachment point coupling the deflection wire to the rack arm, and a linear rack having a first major side and a second major side, the second major side configured to engage the pinion gear, the rack arm extending within the handle obliquely to the longitudinal axis in order to position the linear rack along the pinion gear formed along the circumferential surface offset from the longitudinal axis and position the runners in the guide track in alignment with the longitudinal axis, the attachment point being movable along a linear path that is substantially aligned with the deflection lumen in response to rotation of the pinion gear causing linear movement of the runners in the guide track via the obliquely extending rack arm and linear rack;

wherein rotation of the thumb wheel in a first direction moves the linear rack proximally, via the engagement of the linear rack with the pinion gear, to draw the deflection wire proximally through the deflection lumen and along the guide track inducing a first bend of the catheter body, wherein the rack arm extends through the circumferentially extending slot of the thumbwheel to position the linear rack along the pinion gear, wherein the stationary guide of the handle passes through an arcuate opening of the thumbwheel to interface with the first major surface of the linear rack for holding the second major surface of the linear rack against the pinion gear.

* * * * *